(12) United States Patent
Suzuki (10) Patent No.: US 9,585,570 B2
(45) Date of Patent: Mar. 7, 2017

(54) OBJECT INFORMATION ACQUIRING APPARATUS AND LASER APPARATUS

(71) Applicant: CANON KABUSHIKI KAISHA, Tokyo (JP)

(72) Inventor: Koichi Suzuki, Kodaira (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/306,390

(22) Filed: Jun. 17, 2014

(65) Prior Publication Data
US 2015/0005599 A1 Jan. 1, 2015

(30) Foreign Application Priority Data
Jun. 26, 2013 (JP) .................................. 2013-133910

(51) Int. Cl.
*H01S 3/04* (2006.01)
*A61B 5/00* (2006.01)
(Continued)

(52) U.S. Cl.
CPC ............ *A61B 5/0095* (2013.01); *H01S 3/092* (2013.01); *H01S 3/1305* (2013.01); *H01S 3/1317* (2013.01); *H01S 3/1633* (2013.01); *A61B 5/14542* (2013.01); *H01S 3/0404* (2013.01); *H01S 3/0407* (2013.01); *H01S 3/106* (2013.01); *H01S 3/115* (2013.01); *H01S 3/1625* (2013.01); *H01S 3/1636* (2013.01)

(58) Field of Classification Search
CPC ..... H01S 3/0407; H01S 3/1317; H01S 3/1633
USPC .................................................... 372/34, 35
See application file for complete search history.

(56) References Cited

U.S. PATENT DOCUMENTS 4,272,733 A * 6/1981 Walling .................. H01S 3/106
372/20
5,181,215 A * 1/1993 Sam et al. ...................... 372/34
(Continued)

FOREIGN PATENT DOCUMENTS

| CN | 101286617 | 10/2008 |
|----|-----------|---------|
| CN | 201994556 | 9/2011 |

(Continued)

OTHER PUBLICATIONS

Extended European Search Report issued on Feb. 11, 2015, in counterpart EPA 14171883.3.
(Continued)

*Primary Examiner* — Tod T Van Roy
(74) *Attorney, Agent, or Firm* — Fitzpatrick, Cella, Harper & Scinto (57) ABSTRACT

An object information acquiring apparatus is used which includes: a laser medium; a temperature controlling unit for controlling a temperature of the laser medium; an excitation unit for exciting the laser medium; a control unit for controlling the temperature controlling unit and the excitation unit; a probe for receiving acoustic waves that are generated when an object is irradiated with a laser beam from the laser medium; and a processing unit for acquiring characteristic information relating to the object from the acoustic waves, wherein the control unit does not operate the excitation unit until the temperature of the laser medium falls within a predetermined range.

9 Claims, 8 Drawing Sheets

(51) Int. Cl.
*H01S 3/13* (2006.01)
*H01S 3/092* (2006.01)
*H01S 3/131* (2006.01)
H01S 3/16 (2006.01)
H01S 3/106 (2006.01)
H01S 3/115 (2006.01)
A61B 5/145 (2006.01)

(56) References Cited

U.S. PATENT DOCUMENTS

| | | | |
|---|---|---|---|
| 5,331,652 A * | 7/1994 | Rapoport et al. | 372/34 |
| 5,917,193 A | 6/1999 | Schroff et al. | 250/373 |
| 2003/0058906 A1 * | 3/2003 | Finn et al. | 372/34 |
| 2003/0144713 A1 * | 7/2003 | Furumoto | A61B 18/203 607/89 |
| 2005/0195867 A1 | 9/2005 | Egawa et al. | 372/33 |
| 2005/0200944 A1 * | 9/2005 | Kobayashi | H04B 10/071 359/333 |
| 2006/0239304 A1 * | 10/2006 | Yin et al. | 372/19 |
| 2008/0253416 A1 | 10/2008 | Nishikawa et al. | 372/38.01 |
| 2010/0215066 A1 * | 8/2010 | Mordaunt | A61F 9/008 372/23 |
| 2011/0306865 A1 | 12/2011 | Thornton et al. | 600/407 |
| 2012/0232364 A1 * | 9/2012 | Delmage | 600/311 |
| 2012/0325006 A1 | 12/2012 | Suzuki | 73/655 |

FOREIGN PATENT DOCUMENTS

| | | |
|---|---|---|
| CN | 102223840 | 10/2011 |
| DE | 19600443 A1 | 7/1996 |
| EP | 2737856 | 6/2014 |
| JP | H09-162479 | 6/1997 |
| JP | H11-097769 | 4/1999 |
| JP | 2005-251855 | 9/2005 |
| WO | WO 2012/140864 | 10/2012 |
| WO | WO 2013/018643 | 2/2013 |

OTHER PUBLICATIONS

Chinese (P.R. China) Office Action issued on Nov. 17, 2015 in counterpart application 20141025595.8, with translation.
Chinese (P.R. China) Office Action issued on Nov. 17, 2015 in counterpart application 201410295595.8, with translation.

* cited by examiner

OBJECT INFORMATION ACQUIRING APPARATUS AND LASER APPARATUS

BACKGROUND OF THE INVENTION

Field of the Invention

The present invention relates to an object information acquiring apparatus and a laser apparatus.

Description of the Related Art

Conventionally, photoacoustic apparatuses which cause an object to be irradiated with pulsed light, receive the photoacoustic waves generated inside the object with a probe, and image the form or function inside the object have been researched considerably in the medical field. As a pulse light source of the photoacoustic apparatus, a high-output solid-state laser is used. In order to stabilize the amount of pulsed light of the solid-state laser, it is necessary to stabilize the temperature inside the pulse light source.

Thus, proposed is a laser apparatus that performs a warming-up operation until the temperature inside the pulse light source becomes stable. Patent Literature 1 discloses an apparatus that performs a warming-up operation when the apparatus is turned ON, and determines a correction coefficient of the laser output command value after the temperature inside the light source falls within a predetermined range.

Moreover, a circulator for stabilizing the temperature inside the light source during emission is proposed in Patent Literature 2. With the circulator of Patent Literature 2, stabilization of the laser output is sought by circulating and supplying, to a laser oscillation unit, a cooling medium that is controlled for causing the temperature to be constant.

Moreover, flash lamps are often used as the excitation source of the solid-state laser. By performing Q-switching after causing the flash lamp to emit light and exciting the laser medium, sudden laser oscillation is generated to output a strong laser beam known as a giant pulse.

Patent Literature 1: Japanese Patent Application Laid-Open No. 2005-251855

Patent Literature 2: Japanese Patent Application Laid-Open No. H11-097769 (1999-097769)

SUMMARY OF THE INVENTION

In Patent Literature 1, when the inside of the light source is cold, the time spent on the warming-up operation for heating the inside will be long. When the flash lamp is caused to emit light during that period, it may not be possible to obtain the required output due to the wear of the flash lamp, and the life of the light source may become shortened.

In Patent Literature 2, while the laser is stabilized based on the temperature control of the cooling medium, there is no description regarding the reduction of wear of the flash lamp during the warming-up operation.

The present invention was devised in view of the foregoing problems, and an object of this invention is to provide a laser apparatus capable of reducing the wear of the flash lamp.

The present invention provides an object information acquiring apparatus, comprising:

a laser medium;

temperature controlling means configured to control a temperature of the laser medium;

excitation means configured to excite the laser medium;

control means configured to control the temperature controlling means and the excitation means;

a probe configured to receive acoustic waves that are generated when an object is irradiated with a laser beam from the laser medium; and processing means configured to acquire characteristic information relating to the object in use of the acoustic waves, wherein the control means does not operate the excitation means until the temperature of the laser medium falls within a predetermined range.

The present invention also provides a laser apparatus, comprising:

a laser medium;

temperature controlling means configured to control a temperature of the laser medium;

excitation means configured to excite the laser medium; and control means configured to control the temperature controlling means and the excitation means, wherein the control means does not operate the excitation means until a temperature of the laser medium falls within a predetermined range.

According to the present invention, it is possible to provide a laser apparatus capable of reducing the wear on the flash lamp.

Further features of the present invention will become apparent from the following description of exemplary embodiments with reference to the attached drawings.

DESCRIPTION OF THE EMBODIMENTS

The preferred embodiments of the present invention are now explained with reference to the appended drawings. However, the size, material, shape and relative arrangement of components described below are to be suitably changed depending on the configuration and various conditions of the apparatus to which the present invention is to be applied, and these embodiments are not intended to limit the scope of the present invention to the following descriptions.

The object information acquiring apparatus of the present invention includes an apparatus that uses the photoacoustic effect of receiving acoustic waves generated in an object by causing that object to be irradiated with light (electromagnetic waves), and acquiring the object information as image data.

The object information acquired in the foregoing case indicates the generation source distribution of the acoustic waves that are generated based on light irradiation, the initial sound pressure distribution in the object, the light energy absorption density distribution derived from the initial sound pressure distribution, the absorption coefficient distribution, or the concentration information distribution of substances configuring the tissues. The concentration information distribution of substances is, for example, the oxygen saturation distribution or oxidized/deoxygenated hemoglobin concentration distribution or the like.

The acoustic waves referred to in the present invention are typically ultrasound waves, and include elastic waves referred to as sound waves, ultrasound waves, and acoustic waves. In particular, the acoustic waves that are generated based on the photoacoustic effect are referred to as photoacoustic waves or photoacoustic ultrasonic waves. An acoustic detector (for instance, a probe) receives the acoustic waves that were generated or reflected in the object.

The present invention is unique in being able to reduce the wear of the flash lamp of the laser apparatus. Accordingly, the present invention can be applied not only to an object information acquiring apparatus, but can also be deemed an invention that is related to a laser apparatus. Moreover, the present invention can also be deemed the control method of these apparatuses or the program for causing an information processing apparatus to execute the foregoing control method. In the ensuing explanation, a light source controller is described as a representative example of the laser apparatus.

Embodiment 1

In Embodiment 1, the flash lamp does not emit light until the temperature sensor near the flash lamp falls within a predetermined range.

(Apparatus Configuration)

Figure 1:
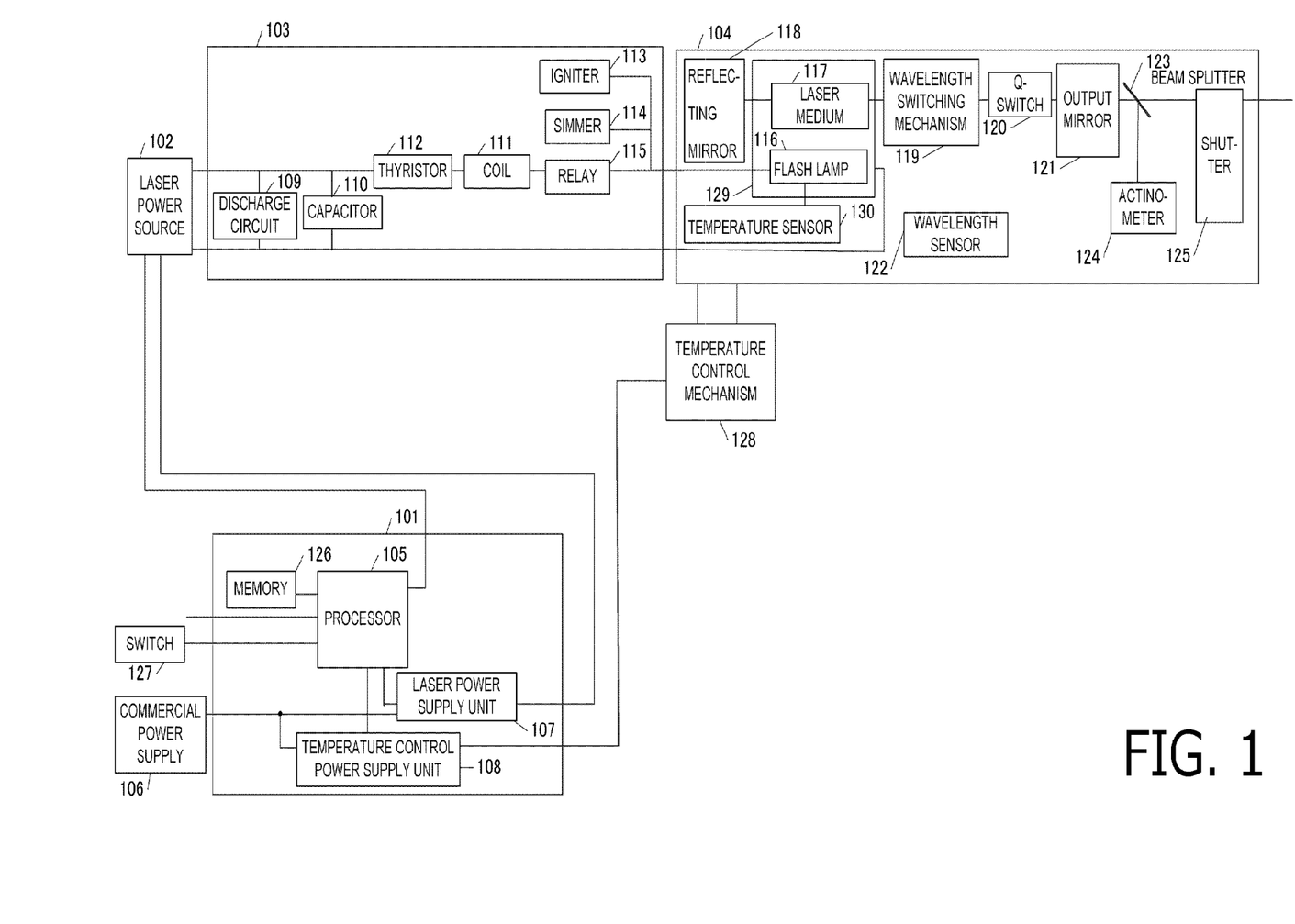
FIG. 1 is a block configuration diagram in Embodiment 1.

FIG. 1 is a block configuration diagram of the light source controller (laser apparatus) in this embodiment. The function and operation of the respective blocks are explained below.

A laser controller 101 controls a laser power source, a laser head and an optical system. The laser controller 101 can receive operations from a user, and can also work under the command of a higher-level controller by being connected thereto. The laser controller corresponds to the control means of the present invention.

A laser power source 102 is a variable voltage power source that supplies an electric charge to a capacitor 110. The laser power source 102 has the function of supplying an electric charge, at a constant current, to the capacitor 110 until the inter-terminal voltage of the capacitor 110 reaches a preset voltage based on a command from the laser controller 101. Moreover, the laser power source 102 has the function of notifying to the laser controller 101 a voltage that is proportional to the inter-terminal voltage of the capacitor 110.

A pulse-forming network 103 accumulates the electric charge from the laser power source 102, and generates a high current pulse for causing a flash lamp 116 to emit light. The pulse-forming network is referred to as "PFN" in the ensuing explanation.

A laser optical system 104 indicates a laser head and an optical system comprising a flash lamp for exciting the laser medium. The laser optical system (and laser head) can output a plurality of wavelengths.

A processor 105 is mounted on the laser controller 101, and controls the various sensors and actuators of the laser power source 102, the PFN 103, and the laser optical system 104 (and laser head). The processor 105 is a semiconductor chip configured from a micro controller and peripheral circuits, and performs emission control, changes parameters such as the light intensity and wavelength, sets and monitors the laser power source voltage, performs shutdown during an abnormality and the like based on software running on the chip. Moreover, the processor 105 performs control for starting, suspending and stopping the operation of the laser power source 102 and a temperature control mechanism 128.

A commercial power supply 106 is a power source of AC 200 V that is input to the laser controller 101. The AC 200 V of the commercial power supply 106 is converted into a DC voltage by the DC power supply (not shown) inside the laser controller 10 and used for activating the processor 105. Moreover, the commercial power supply 106 is distributed to the laser power source 102 and the temperature control mechanism 128 via the laser controller 101.

A laser power supply unit 107 is a circuit for supplying the commercial power supply 106 to the laser power source 102 based on a signal from the processor 105, and is configured from a relay and an output connector. By controlling the short-circuit and release of the relay from the processor 105, the activation and stopping of the laser power source 102 can be controlled.

A temperature control power supply unit 108 is a circuit for supplying the commercial power supply 106 to the temperature control mechanism 128 based on a signal from the processor 105, and is configured from a relay and an output connector. By controlling the short-circuit and release of the relay from the processor 105, the activation and stopping of the temperature control mechanism 128 can be controlled.

A discharge circuit 109 is a circuit for discharging the electric charge accumulated in the capacitor 110, and is configured from a relay and a current limiting resistor. The electric charge of the capacitor 110 can be discharged by short-circuiting the relay based on a control signal from the processor 105.

A capacitor 110 accumulates the electric charge for causing the flash lamp 116 to emit light. A high-voltage, large-capacity film capacitor or the like is used as the capacitor 110.

A coil 111 shapes the pulsed current waveform from the capacitor.

A thyristor 112 controls whether to cause the electric charge of the capacitor 110 to flow to the flash lamp 116 in the laser optical system 104 based on a control signal from the processor 105.

An igniter 113 applies a high voltage to the flash lamp 116 based on a control signal from the processor 105, and forms a conducting path. The igniter circuit is configured from a high voltage DC-DC converter and a current limiting resistor.

A simmer circuit 114 is a circuit for causing a constant standby current to flow to the flash lamp 116 in order to maintain the conducting path formed in the flash lamp 116. The simmer circuit 114 is configured from a constant current circuit and a backflow prevention diode.

A high voltage relay 115 blocks the thyristor 112 from the flash lamp 116 while the igniter 113 is applying a high voltage to the flash lamp 116. As a result of the processor 105 sending a control signal to the thyristor 112 in a state where a standby current is flowing to the flash lamp 116 and the high voltage relay is short-circuited, the electric charge of the capacitor 110 is transferred to the flash lamp 116, and the flash lamp 116 emits light.

The flash lamp 116 emits excitation light for exciting the laser medium. The flash lamp corresponds to the excitation means of the present invention.

Reference numeral 117 to reference numeral 121 are components configuring the laser resonator.

A laser medium 117 is a crystal such as YAG, titanium sapphire, or alexandrite disposed near the flash lamp. In this embodiment a case of using alexandrite is explained. An alexandrite laser yields higher luminous efficiency and greater optical output at a temperature that is higher than normal temperature. Thus, the temperature of the laser medium needs to be maintained at a temperature that is higher than normal temperature. Thus, the temperature control mechanism 128 uses a circulator and causes a fluid substance such as water of approximately 80 degrees Celsius to circulate near the laser medium so as to maintain the required temperature for obtaining sufficient optical output.

Reference numeral 118 is a reflecting mirror.

A wavelength switching mechanism 119 is configured from a birefringent filter and an activating motor. The birefringent filter can be operated and one resonating wavelength can be selected among a plurality of wavelengths based on a control signal from the processor 105. This embodiment explains a case of selecting one wavelength from two types of wavelengths. These wavelengths are hereinafter respectively referred to as a first wavelength and a second wavelength in the ensuing explanation. When a laser apparatus capable of generating a plurality of wavelengths is applied to an object information acquiring apparatus, the substance concentration in the object can be acquired as characteristic information.

The electrooptic element 120 performs Q-switching based on a control signal from the processor 105.

Reference numeral 121 is an output mirror.

A wavelength sensor 122 is mounted on the wavelength switching mechanism 119, and outputs to the processor 105 a signal indicating the currently selected wavelength. A high level voltage is output when the position of the wavelength switching mechanism 119 is at a position corresponding to the first wavelength, and a low level voltage is output when the position of the wavelength switching mechanism 119 is at a position corresponding to the second wavelength.

The beam splitter 123 branches a part of the laser beam that was output via the output mirror 121, and causes that branched laser beam to enter an actinometer 124. However, most of the light takes a straight line and enters the shutter 125. The actinometer corresponds to the light intensity measuring means of the present invention.

The actinometer 124 is a circuit for measuring the energy for each pulse notifying the result to the processor 105, and is configured from a pyroelectric sensor or a photodiode and an amplifier circuit.

A shutter 125 switches to impellent selection between whether to output the laser beam outward based on a control signal from the processor 105 or not.

A memory 126 is a nonvolatile memory for storing various setting parameters. For example, let it be assumed that a correspondence relation of the voltage to be output by the laser power source 102 and the light intensity output by the light source is calibrated in advance for each wavelength, and stored in the memory 126. Consequently, when the user designates the light intensity and wavelength to be output, the processor 105 can estimate and set the voltage to be set in the laser power source 102.

A switch 127 is a switch with a key that is used for activating the light source.

A temperature control mechanism 128 is a mechanism for stabilizing the temperature near the laser medium. The temperature control mechanism 128 comprises a pump for circulating water of a constant temperature in the chassis housing the laser medium 117 and the flash lamp 116. The temperature control mechanism 128 internally comprises an electrothermal heater, a cooling fan, a thermometer, and a temperature controller. The temperature controller measures the temperature of the circulating water using a thermometer, and controls the water temperature to be maintained at 80 degrees using a heater and a cooling fan. When the water temperature is around 20 degrees as with the room temperature immediately after activation, the water is heated to 80 degrees with the electrothermal heater. During the laser emission, apart of the energy of the flash lamp turns into heat and the water temperature attempts to reach 80 degrees or higher, but control is performed using a cooling fan so that the water temperature does not considerably exceed 80 degrees. The temperature control mechanism corresponds to the temperature controlling means of the present invention.

A lamp house 129 is a housing that houses the flash lamp 116 and the laser medium 117 near each other in a single housing. By disposing the flash lamp 116 and the laser medium 117 near each other, the excitation light of the flash lamp is efficiently absorbed by the laser medium, and energy that is lost as heat can be reduced.

A temperature sensor 130 is mounted on the lamp house. As the temperature sensor, there may be used a thermocouple, a thermistor, an infrared temperature sensor or the like. A signal from the temperature sensor 130 is input to the processor 105. The processor controls the operation of the temperature control mechanism 128 and the laser power source 102 based on temperature information. Specifically, the temperature control mechanism 128 is activated but the laser power source 102 is not activated until the temperature of the laser medium nears 80 degrees. Once the temperature is stabilized near 80 degrees, the laser power source is activated to emit light from the flash lamp, and the actinometer 124 is used for confirming whether the light intensity is stable. Subsequently, while the operation of the temperature control mechanism 128 is continued until the object to be actually irradiated with the laser is set up, the emission of the flash lamp is stopped, and a simmer current is caused to flow. After the setup of the object is complete, the laser power source is activated and light is emitted from the flash lamp, the actinometer 124 is used for confirming the light intensity is stable, and the object is thereby irradiated with the laser.

(Processing Flow)

Figure 2:
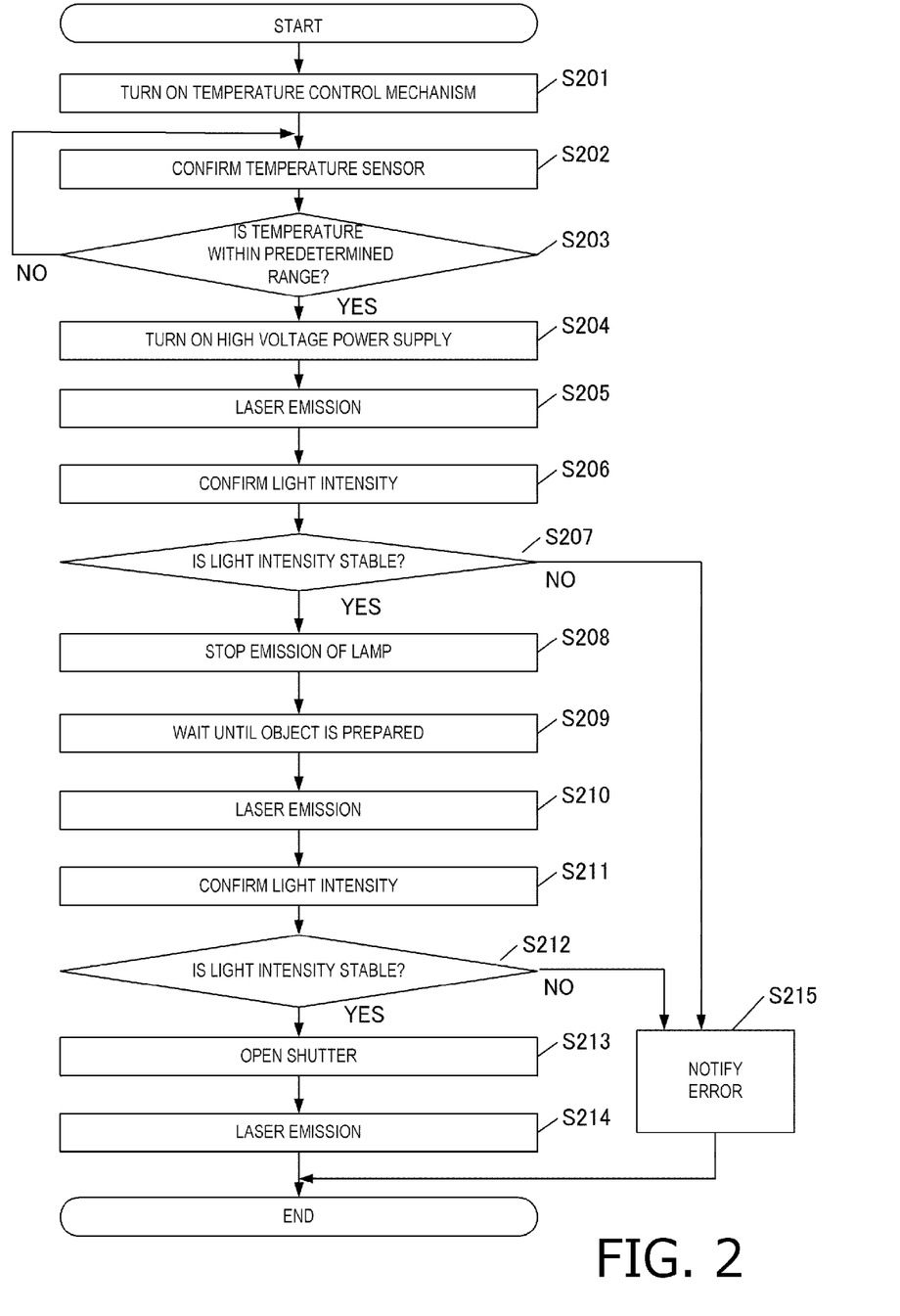
FIG. 2 is an operational flowchart in Embodiment 1.

FIG. 2 is an operational flowchart of the activation and operation of the light source upon using the laser controller of the present invention.

When the user turns on the switch 127 attached to the laser controller, in step S201, the processor 105 sends a control command to the temperature control power supply unit 108, and starts supplying the commercial power supply 106 to the temperature control mechanism 128. The operation of the temperature control mechanism 128 is thereby started, and the heating of water by the electrothermal heater is started. In other words, the electrothermal heater corresponds to the heating means of the present invention.

Subsequently, in step S202, the processor 105 reads the signal from the temperature sensor 130 and calculates the temperature.

Subsequently, in step S203, the processor 105 determines whether the temperature of the temperature sensor 130 is within a predetermined range. A predetermined range in this embodiment is a case where the temperature is 80 degrees or higher. When the temperature is 80 degrees or higher (S202=YES), it is determined that the laser medium 117 has been sufficiently warmed, and the routine proceeds to step S204. Meanwhile, when the temperature is lower than 80 degrees (S202=NO), the routine returns to step S202, and, after the lapse of a given period of time, a signal of the temperature sensor 130 is once again read and the temperature is calculated.

Subsequently, in step S204, the high voltage power source is turned ON. In other words, the processor 105 sends a control command to the laser power supply unit 107, and starts supplying the commercial power supply 106 to the laser power source 102. The laser power source is thereby activated.

Subsequently, in step S205, the laser controller 101 controls the laser power source 102, the PFN 103 and the laser optical system 104, and thereby emits laser light. The operational flow of laser emission will be described later.

Note that, in step S205, the processor 105 keeps the shutter 125 closed to prevent the laser beam from being output outside the laser optical system 104. A part of the laser beam is input to the actinometer 124.

Subsequently, in step S206, the processor 105 sends a signal to the actinometer 124, reads the light intensity value for each pulse, and stores the result in the memory of the processor 105.

Subsequently, in step S207, whether the light intensity value of a prescribed period is stable within a predetermined range is confirmed. When a state where the light intensity is within a predetermined range continues (S207=YES), the warming-up is deemed complete since the pulsed light is sufficiently stable, and the routine proceeds to step S208. Meanwhile, when the light intensity does not fall within a predetermined range within a predetermined time (S207=NO), it is determined that the pulsed light cannot be stabilized even when sufficient warming-up is performed, and the routine proceeds to step S215.

In step S208, the laser controller 101 enters a standby state since the warming-up is deemed complete. A control command is sent to the laser power source 102 and the PFN 103, and the charge/discharge of the capacitor 110 and the emission of the flash lamp 116 are stopped. Meanwhile, a control command is sent to the simmer circuit 114, and a standby current is caused to flow to the flash lamp 116.

Subsequently, in step S209, the laser controller 101 stands by until the object is prepared. The preparation of an object refers to the user setting up an object at a position to be irradiated with a laser beam, setting the irradiation position and number of pulses, and giving an instruction for starting the laser irradiation. The processor 105 proceeds to step S210 upon receiving a laser irradiation start instruction from the switch 127 or a higher-level controller.

In step S210, the laser controller 101 controls the laser power source 102, the PFN 103 and the laser optical system 104, and thereby emits a laser pulse as in step S205.

Subsequently, in step S211, the processor 105 sends a signal to the actinometer 124 and reads the light intensity value for each pulse, and stores the result in the memory of the processor 105. Subsequently, in step S212, whether the light intensity value of a prescribed period is stable within a predetermined range is confirmed as in step S207. When it is determined that the pulsed light is stable (S212=YES), the routine proceeds to step S213. Meanwhile, when it is determined that the pulsed light cannot be stabilized even upon performing sufficient warming-up (S212=NO), the routine proceeds to step S215.

Subsequently, in step S213, the processor 105 sends a control command to the shutter 125, and opens the shutter.

Subsequently, in step S214, the laser is emitted for irradiating the object. In addition, after a laser of a pre-set number of pulses is emitted, the laser power source 102 and the temperature control mechanism 128 are stopped, and the processing is ended.

Meanwhile, in step S215, the processor 105 notifies an error to the user and the higher-level controller to the effect that the light intensity cannot be stabilized, and thereafter stops the laser power source 102 and the temperature control mechanism 128, and ends the processing.

(Structure of Laser Power Source)

Figure 3:
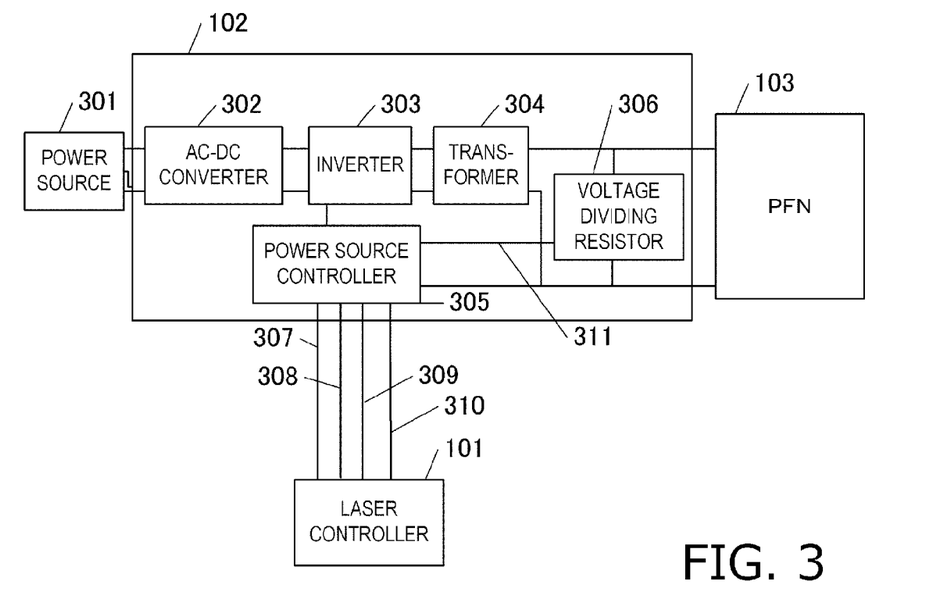
FIG. 3 is a block configuration diagram of the laser power source in Embodiment 1.

FIG. 3 is a block diagram showing the internal structure of the laser power source 102.

A power source 301 is a power source of AC 200 V supplied from the laser power supply unit 107.

An AC-DC converter 302 converts the AC 200 V into a direct current.

An inverter 303 converts the direct current into an alternating current.

A transformer 304 boosts the voltage from the inverter.

A power source controller 305 turns ON/OFF the FET not shown in the inverter, and controls the DUTY ratio of the inverter output in order to output a constant current to the PFN 103.

A voltage dividing resistor 306 divides the voltage that was boosted with the transformer 304, and feeds back the divided voltage to the power source controller.

A signal 311 that is fed back by the voltage dividing resistor 306 is referred to as a feedback signal. Moreover, an output start signal 307, a voltage setting signal 308, an output completion signal 309, and a monitor signal 310 are interfaces between the power source controller and the laser controller.

The output start signal 307 is a one-bit digital signal, and, when the laser controller 101 is outputting a high level, the power source controller 305 operates the inverter 303 and supplies a constant current to the PFN 103. Meanwhile, when the laser controller 101 of FIG. 1 is outputting a low level, the power source controller 305 stops the inverter 303.

The voltage setting signal 308 is an analog signal in the range of 0 V to 10 V, and is used for setting the amount of electric charge to be accumulated in the capacitor 110. The electric charge is supplied to the capacitor 110 in the PFN 103 until the inter-terminal voltage of the capacitor 110 becomes a voltage that is proportional to the voltage of the voltage setting signal 308. The power source controller 305 activates the inverter 303 and charges the capacitor 110 when the voltage of the feedback signal 311 is smaller than the input voltage from the voltage setting signal 308. Meanwhile, the power source controller 305 stops the inverter 303 when the voltage of the feedback signal 311 is equal to or greater than the voltage of the voltage setting signal 308.

The output completion signal 309 is a one-bit digital signal, and is a signal indicating whether the electric charge is being accumulated in the capacitor 110, or whether the charging is complete. When the voltage of the feedback signal 311 is smaller than the voltage of the voltage setting signal 308, the power source controller 305 determines that charging is being performed, and changes the output completion signal to a high level. Meanwhile, when the voltage of the feedback signal 311 is equal to or greater than the voltage of the voltage setting signal 308, the power source controller 305 determines that the charging is complete, and changes the output completion signal 309 to a low level.

The monitor signal 310 is an analog signal in the range of 0 V to 10 V, and a voltage that is proportional to the inter-terminal voltage of the capacitor 110 is output from the laser power source 102 to the laser controller 101. The power source controller 305 performs noise reduction and impedance conversion based on the voltage of the feedback signal 311, and outputs the result to the laser controller 101.

(Structure of Temperature Control Mechanism)

Figure 4:
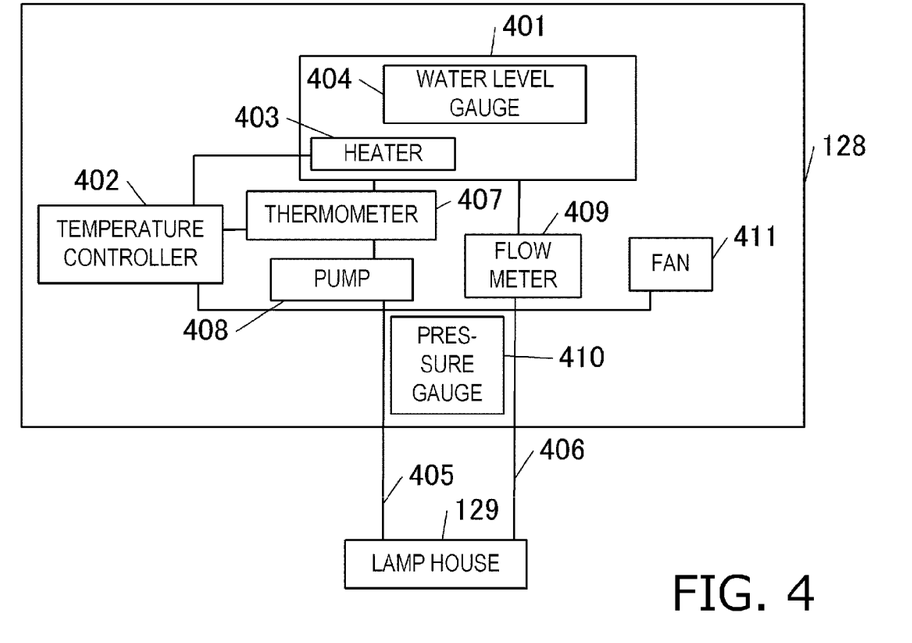
FIG. 4 is a block configuration diagram of the temperature control mechanism in Embodiment 1.

FIG. 4 is an internal block configuration diagram of the temperature control mechanism 128.

A water tank 401 is a container for storing water.

A temperature controller 402 controls the water temperature to be a preset temperature.

An electrothermal heater 403 heats the water. The current of the electrothermal heater can be controlled from the temperature controller 402.

A water level gauge 404 measures the water level in the water tank 401.

A water pipe 405 supplies water from the water tank 401 to the lamp house 129. In addition, water returns to the water tank 401 from the lamp house 129 via the water pipe 406.

A thermometer 407 measures the water temperature in the water pipe 405. The temperature controller 402 monitors the water temperature of the water pipe 405 by referring to the measurement result of the thermometer 407. The thermometer corresponds to the temperature measuring means of the present invention.

Moreover, a pump 408 circulates water through the path of the water tank 401, the water pipe 405, the flash lamp 116, and the water pipe 406.

A flow meter 409 measures the flow rate of water in the water pipe 406.

A pressure gauge 410 measures the water pressure in the water pipe 405. The temperature controller 402 monitors the values of the water level gauge 404, the flow meter 409, and the pressure gauge 410, displays a warning when the water level is outside a predetermined range, and stops the pump 408. Moreover, in the foregoing case, the temperature controller 402 communicates with the laser controller 101 and notifies an error.

Moreover, a fan 411 cools the water of the water pipe 406. The rotation of the fan can be controlled with the temperature controller 402. The temperature controller 402 reads the value of the thermometer 407, and performs feedback control of the current of the electrothermal heater 403 and the rotation of the fan 411 so that the value coincides with the temperature setting value from the laser controller 101. As the control algorithm, PID control is performed based on a measurement error between the temperature setting value and the thermometer 407.

As described above, the temperature control mechanism 128 performs temperature control of the laser medium by controlling the water temperature when the flash lamp 116 and the laser medium 117 are stored in the lamp house 129.

(Processing Flow of Laser Emission)

Figure 5:
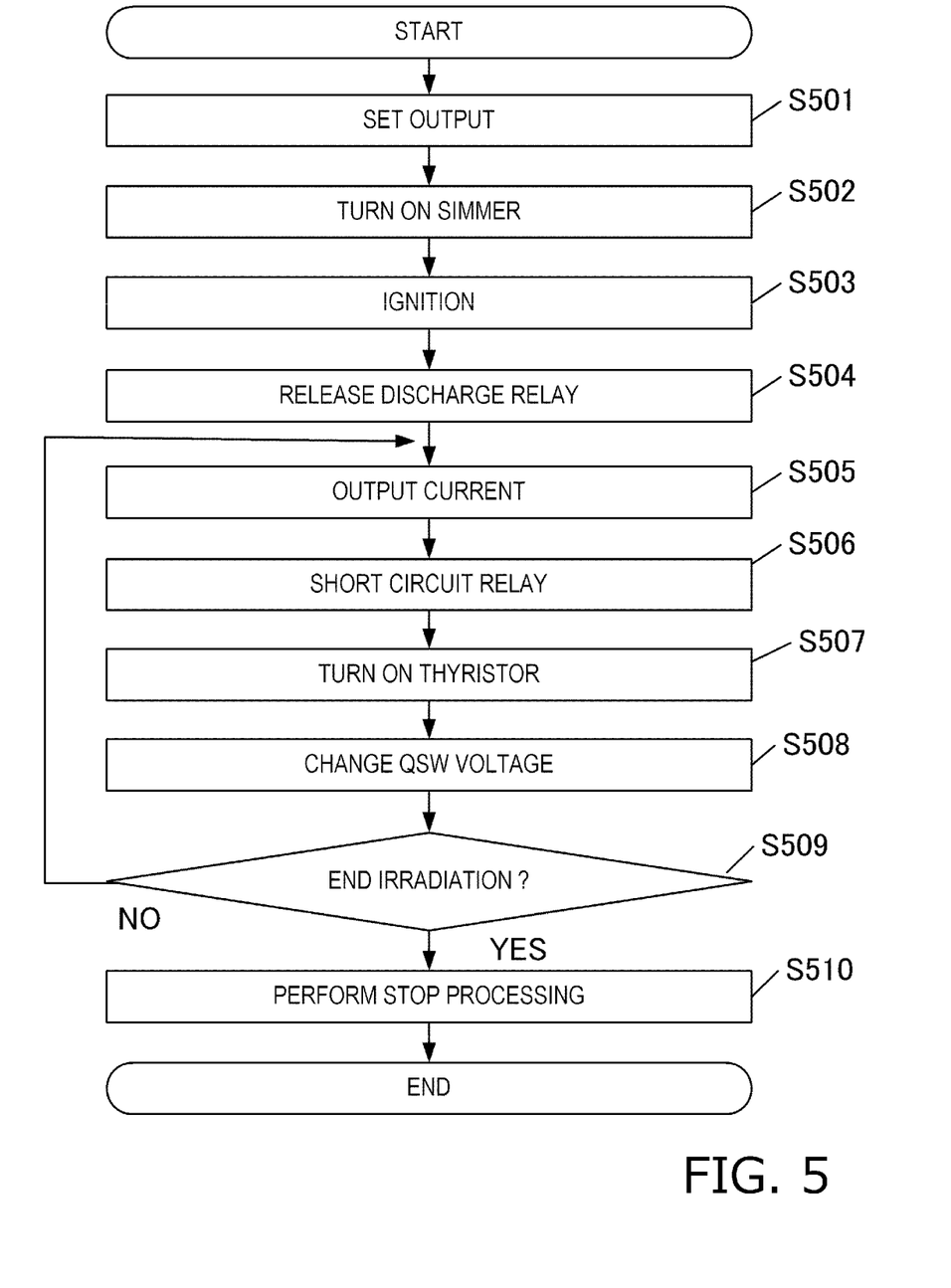
FIG. 5 is an operational flowchart of the laser emission in Embodiment 1.

FIG. 5 is a diagram showing the operational flowchart of laser emission. This diagram is the operational flow when the laser controller repeatedly emits pulsed light.

In step S501, the processor 105 sets the output. In other words, the processor 105 reads the light intensity and wavelength set by the user, and sets the voltage value in the laser power source 102. Let it be assumed that the relation of the light intensity and the voltage is recorded in the memory 126. Moreover, the processor 105 sends a control command to the wavelength switching mechanism 119 based on the wavelength set by the user, and selects the birefringent filter for outputting the set wavelength. When the operation of the wavelength switching mechanism is complete, the wavelength sensor 122 outputs to the laser controller 101 a signal indicating the selected wavelength.

Moreover, in step S501, the processor 105 reads the number of repetitions of the pulsed light set by the user, and internally stores that number.

Subsequently, in step S502, the processor 105 sends a control signal to the simmer circuit 114, and starts outputting a current from the simmer circuit. However, since a conducting path is not formed in the flash lamp 116 at this stage, the simmer current will hardly flow to the flash lamp 116.

Subsequently, in step S503, when a conducting path is not formed in the flash lamp 116, the processor 105 sends a control signal to the igniter circuit 113, and applies a high voltage to the flash lamp 116. This operation is referred to as "ignition". Consequently, the flash lamp 116 is discharged, a conducting path is formed therein, and the current output from the simmer 114 flows to the flash lamp 116. Note that whether a conducting path is formed in the flash lamp is determined based on whether the simmer circuit 114 is causing a simmer current to flow to the flash lamp.

Subsequently, in step S504, the processor 105 sends a control signal to the discharge circuit 109, and releases the relay of the discharge circuit. Consequently, the positive-side terminal and the negative-side terminal of the capacitor 110 are released, and an electric charge can be accumulated in the capacitor 110.

Subsequently, in step S505, the processor 105 sends a control signal to the laser power source 102, and causes a constant current to be output to the capacitor 110. Consequently, an electric charge is accumulated in the capacitor 110 at a constant ratio, and the inter-terminal voltage of the capacitor 110 will rise. The laser power source 102 stops the current output at the time that the inter-terminal voltage of the capacitor 110 reaches the voltage that was set in step S501.

In step S506, the processor 105 sends a control signal to the relay 115, and short-circuits the connection between the thyristor 112 and the flash lamp 116.

Subsequently, in step S507, the processor 105 sends a control signal to the thyristor 115 and turns ON the thyristor. Consequently, the gap from the capacitor 110 to the flash lamp 116 is connected via the coil 111. The electric charge accumulated in the capacitor 110 flows to the flash lamp 116, and light is emitted from the flash lamp 116. When the electric charge accumulated in the capacitor 110 runs out, the thyristor 115 is turned OFF. Moreover, the light from the flash lamp 116 is absorbed by the laser medium 117, and the laser medium 117 excited.

Subsequently, in step S508, the processor 105 sends a control signal to the Q-switch driver circuit not shown several 100 microseconds after the excitation, and reduces the loss of the Q-switch (QSW), which was theretofore in a state of great loss, to be a small loss. This is performed by changing the inter-terminal voltage of the electrooptic element from a high voltage to a low voltage. Consequently, sudden laser oscillation will occur, and a giant pulse is output from the output mirror 121.

Subsequently, in step S509, it is determined whether the laser emission for the number of times set in step S501 is complete. When complete (S509=YES), the routine proceeds to step S510. Meanwhile, when incomplete (S509=NO), the routine proceeds to step S505, and an electric charge is once again accumulated in the capacitor 110.

In step S510, the processor 105 closes the shutter 125 and sends a control signal to the relay 115, and releases the thyristor 112 and the flash lamp 116. Moreover, the processor 105 sends a control signal to the discharge circuit 109, and short-circuits the terminals of the capacitor 110 via the current limiting resistor in the discharge circuit. The electric charge remaining in the capacitor 110 is thereby discharged.

(Timing of Operation and Emission Period)

Figure 6A:
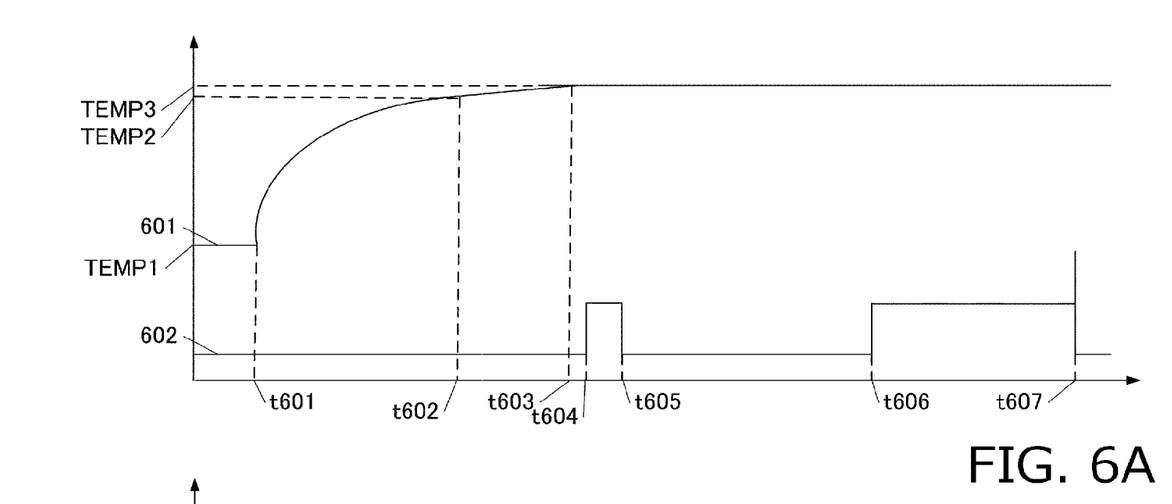
FIGS. 6A and 6B are diagrams showing the time change of the temperature and power consumption in Embodiment 1.
Figure 6B:
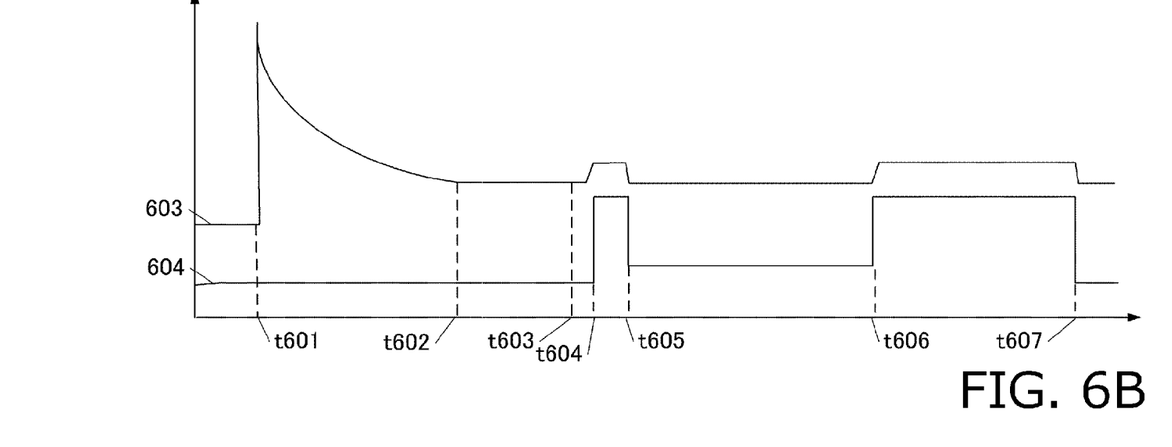

FIG. 6A is a diagram showing the time change of the temperature near the lamp house 129 detected with the temperature sensor 130 and the operating time of the flash lamp 116. FIG. 6B is a diagram showing the time change of the laser emission power supplied to the laser power source 102 and the temperature control power supplied to the temperature control mechanism 128.

Foremost, the operational flow from the warming-up to the irradiation of the object with a laser, and the temperature of the lamp house 129 and the emission time of the flash lamp 116 are explained with reference to FIG. 6A.

In FIG. 6A, a graph 601 shows the time change of the temperature near the lamp house 129. The vertical axis represents the temperature, and the horizontal axis represents the time. A graph 602 shows the operating time of the flash lamp 116. The graph shows that operation in the vertical axis is a high level, and no operation in the vertical axis is a low level. The horizontal axis represents the time.

At time t601, the laser controller 101 starts the warming-up. Time t601 corresponds to step S201 of FIG. 2. At this stage, the temperature near the lamp house 129 is around 20 degrees (TEMP1), which is the same as the room temperature. When the temperature control mechanism 128 starts the operation in step S201, the temperature controller 402 starts applying electricity to the electrothermal heater 403 since the value of the thermometer 407 is lower than the preset temperature of 80 degrees (TEMP3). Consequently, the water in the water tank 401 is heated, supplied to the flash lamp 116 by the pump 408, and the temperature of the lamp house thereby gradually increases.

The time that the scale reading of the thermometer 407 basically reaches the preset temperature is referred to as t602. From time t602 onward, the temperature controller 402 controls the current of the electrothermal heater 403 so as to maintain the water temperature at the preset temperature. At this stage the water temperature is approximately 80 degrees, but since it takes time for heat to be transmitted to the lamp house 129, the scale reading of the temperature sensor 130 will be a value (TEMP2) that is lower than 80 degrees.

While the water of the preset temperature is being circulated, heat will be sufficiently transmitted to the lamp house 129, and, at time t603, the value of the temperature sensor 130 exceeds the preset temperature. Then, the routine proceeds to the processing of step S204, and the power source of the laser power source 102 is turned ON. The laser medium 117 and the flash lamp 116 are housed in the lamp house 129, and, since the temperature of the laser medium 117 is stable at 80 degrees at this stage, it is determined that the preparation for laser emission is complete.

At time t604, the laser emission and the light intensity are confirmed based on step S205 and step S206. When the light intensity is stable after emitting the laser for a predetermined number of pulses, the emission of the flash lamp is stopped in step S208 and step S209, and flash lamp stands by until the preparation of the object is complete.

When the preparation of the object is complete at time t606, the laser emission and the light intensity are confirmed based on step S210 and step S211. When the light intensity is stable after emitting the laser for a predetermined number of pulses, the object is irradiated with the laser in step S213 and step S214.

After emitting the laser for a predetermined number of pulses, the flash lamp is stopped at time t607.

As described above, the only time that the flash lamp emits light during the operation from the warming-up to the laser irradiation is only between time t604 and time t605, and between time t606 and time t607. The flash lamp 116 does not emit light during the heating time of the laser medium 117 (t601 to t603) and the preparation time of the object (t605 to t606), which take time. It is thereby possible to reduce the wear of the flash lamp, and extend the life of the flash lamp.

Moreover, during the period from time t603 to time t607, the temperature of the laser medium 117 is maintained near the preset temperature by the circulating water from the temperature control mechanism 128.

(Timing of Operation and Power Consumption)

Moreover, the present invention yields an effect of being able to reduce the peak of power consumption, even though it takes time to perform the warming-up, in comparison to the case of simultaneously activating the excitation means and the temperature controlling means during the warming-up. This effect is now explained with reference to FIG. 6B.

In FIG. 6B, a graph 603 shows the power consumption of the temperature control mechanism 128, and a graph 604 shows the power consumption of the laser power source 102. The vertical axis represents the power consumption, and the horizontal axis represents the time. Note that, in FIG. 6B, the origins of the vertical axis of the graph 603 and the graph 604 are displaced for easier viewing.

From time t601 to time t602, power is mainly consumed by the electrothermal heater 403 that heats the water of the water tank 401 of the temperature control mechanism 128. Since the difference between the water temperature (TEMP1) and the preset temperature (TEMP3) is considerable immediately after the operation of the temperature controller 402 is started, the temperature controller 402 attempts to heat the water quickly by causing a large current to flow to the electrothermal heater 403. As the water temperature gradually rises and the difference with the target temperature decreases, the current that is caused to flow to the electrothermal heater 403 by the temperature controller 402 becomes smaller. The power consumption of the graph 603 also decreases accordingly.

From time t602 to time t603 and from time t605 to time t606, in order to maintain the water temperature at the temperature setting value, the temperature controller 402 causes a small current to flow to the electrothermal heater 403 and the fan 411. Moreover, the pump 408 is operated to maintain the circulation of water. During these periods, the power consumption is basically constant and lower than during the heating of water.

From time t604 to time t605 and from time t606 to time t607, since a part of the energy becomes heat when the flash lamp 116 emits light, the lamp house 129 is heated. In order to cool the lamp house 129 and maintain a constant temperature, the temperature controller 402 performs control in which the current consumption of the fan 411 increases and, therefore, the power consumption of the temperature control mechanism 128 will slightly increase.

Meanwhile, the power consumption of the laser power source 102 is zero since a power source is not supplied from the laser power supply unit 107 between time t601 and time t603.

From time t603 to time t604, while the power source controller 305 and the AC-DC converter 302 are operated, the inverter 303 and the transformer 304 are not operated and in an idle state. The power consumption during this period slightly increases.

From time t604 to time t605 and from time t606 to time t607, the operation according to the routine shown in FIG. 5 is performed. In other words, the inverter 303 and the transformer 304 are operated for causing the flash lamp 116 to emit light, charge/discharge is performed to the capacitor 110, and the igniter circuit 113 and the simmer circuit 114 are also operated. During this period, the power consumption of the laser power source 102 will increase.

From time t605 to time t606, the charge/discharge to the capacitor 110 is not performed. However, in order to cause the flash lamp 116 to emit light as soon as the preparation of the object is complete, the simmer circuit 114 is activated, and a simmer current is caused to flow. Thus, while the power consumption will increase for the amount of causing the simmer current to flow in comparison to the idle state, the power consumption is lower in comparison to the case of causing the flash lamp to emit light.

As shown in the graph 603 and the graph 604, the time (t601 to t602) when the power consumption of the temperature control mechanism 128 is great and the time (t604 to t605 and t606 to t607) when the power consumption of the laser power source 102 is great do not overlap. It is thereby possible to lower the peak of power consumption of the overall light source apparatus, and enable the downsizing of the power source system and reduction of costs.

Moreover, upon heating the laser medium 117, preferably, most of the power that can be supplied from the commercial power supply 106 to the light source is assigned to the temperature control mechanism 128, and most of the power that can be used during the laser emission is assigned to the laser power source 102. It is thereby possible to obtain a high laser beam output with less commercial power supply equipment.

Note that, in this embodiment, while the temperature control and the temperature measurement were collectively performed in the lamp house 129 housing the flash lamp 116 and the laser medium 117, the present invention is not limited thereto. For example, in a configuration where the laser medium and the flash lamp are separated, the present invention can be applied by individually performing the temperature control and the temperature measurement.

Moreover, while this embodiment explained a case of causing a simmer current to flow to the flash lamp 116 while the object is being prepared, the operation to be performed during the preparation is not limited thereto. When the preparation time of the object is long, the simmer current may once be stopped, and the igniter may be operated once the preparation is complete to perform a discharge. It is thereby possible to reduce the power consumption during the preparation period.

Moreover, while this embodiment explained a case of not emitting light from the flash lamp until the temperature sensor 130 rises to a preset temperature, it is also possible to operate only the temperature control mechanism partway, and subsequently perform the temperature control and flash lamp emission simultaneously. For example, the temperature controlling means is operated until reaching a temperature (TEMP2) that is lower than the preset temperature, and the flash lamp may emit light from t602 to t603. While this will increase the wear on the flash lamp, the time required until the lamp house 129 is heated can be shortened. Moreover, the flash lamp emission can also be started from a temperature between TEMP1 and TEMP2.

Moreover, while this embodiment determined that the temperature of the laser medium is table when the temperature is equal to or greater than the threshold in step S203, the determination method of whether the temperature is stable is not limited to the simple comparison of thresholds. For example, it is also possible to determine that the temperature of the laser medium is stable when a state in which the temperature sensor is within a range of 80 degrees to 85 degrees continues for a given period of time or longer.

Moreover, while this embodiment determines that the light intensity is stable when a state where the light intensity is within a certain range continues for a given period in step S212, the method of determining whether the light intensity is stable is not limited thereto. For example, it is also possible to calculate the average value and scattering of the light intensity during a certain period, and determine that the light intensity is stable when the average value is within a certain range and the scattering is not greater than a given value.

Moreover, while this embodiment performs the electrification and blockage of the power source by the laser power supply unit 107 and the temperature control power supply unit 108 as the method of realizing the start and stop of operations of the laser power source 102 and the temperature control mechanism 128, and activation/stopping method is not limited thereto. For example, a separate control line may be provided to the power source controller 305 and the temperature controller 402, and the operation start/stop control may be realized by sending a control signal from the processor 105.

Moreover, in this embodiment, while the temperature control mechanism 128 controlled the water temperature by subjecting the electrothermal heater 403 to PID control, the method of controlling the water temperature is not limited thereto. For example, it is also possible to use a heat pump in substitute for the electrothermal heater to further improve the efficiency, and to further reduce power consumption.

As explained above, the light source controller (laser apparatus) of the present invention can reduce the wear of the flash lamp and extend of the life of the flash lamp by causing the flash lamp not to emit light until the laser medium is heated. Moreover, in comparison to the case of simultaneously activating the excitation means and the temperature controlling means during the warming-up, the peak of power consumption of the overall light source can be reduced, the power source system can be downsized, and costs can be reduced.

Embodiment 2

An example of a system in which a light source controller (laser apparatus) is applied to a photoacoustic apparatus (object information acquiring apparatus) is now explained as Embodiment 2 of the present invention.

(Apparatus Configuration)

Figure 7:
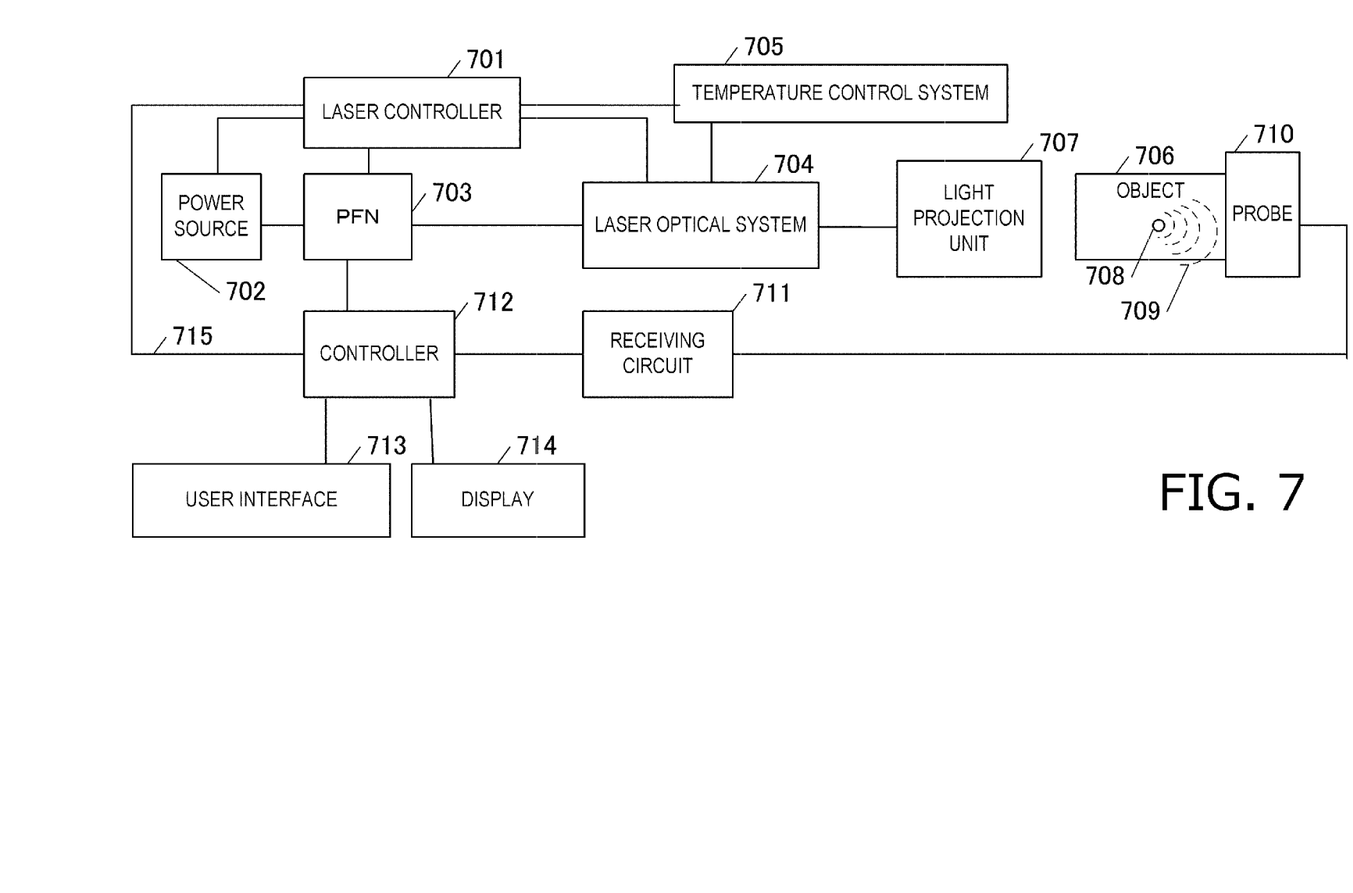
FIG. 7 is a block configuration diagram in Embodiment 2.

FIG. 7 is a block configuration diagram of the photoacoustic apparatus. In FIG. 7, since a laser controller 701, a laser power source 702, a PFN 703, a laser optical system 704, and a temperature control system 705 respectively correspond to the laser controller 101, the laser power source 102, the PFN 103, the laser optical system 104, and the temperature control mechanism 128 of Embodiment 1, the detailed explanation thereof is omitted.

An object 706 is the target to be measured by the photoacoustic apparatus, and is a part of the test subject's body. Here, the object is a breast as a part of the living body. The light projection unit 707 irradiates the measurement segment of the object with pulsed light.

A light projection unit 707 includes an optical system for expanding the light emitted from the laser optical system at a predetermined magnification, and adjusting the density and irradiation region of the irradiation light. The transmission of light from the laser optical system 704 to the light projection unit 707 is performed via a bundle fiber or space transmission.

A light absorber 708 represents a segment with significant light absorption that exists within the object and, for example, corresponds to a newborn blood vessel caused by breast cancer in the present case. When the light absorber 708 is irradiated with pulsed light, photoacoustic waves 709 are generated based on the photoacoustic effect.

A probe 710 internally comprises an oscillator for receiving the photoacoustic waves 709. The oscillator is configured by arranged ultrasonic sensor elements such as PZT or CMUT in an array, and converts photoacoustic waves 709 into electrical signals. These electrical signals are referred to as photoacoustic signals.

A receiving circuit 711 receives the photoacoustic signals from the probe 710. The receiving circuit 711 is configured from a preamplifier, an A/D converter, a receiving memory, and an FPGA. The photoacoustic signals are amplified with the preamplifier, converted into a digital value with the A/D converter, and then input to the FPGA. FPGA performs signal processing such as noise reduction processing and phasing. The photoacoustic signals that were subject to signal processing in the receiving circuit are stored in a memory not shown. The data stored in the memory is referred to as the photoacoustic signal data.

A controller 712 controls the operation of the overall photoacoustic apparatus. The controller 712 is configuring from an image processing circuit of a personal computer or a GPU. The image processing circuit reads the photoacoustic signal data and performs image reconfiguration processing, generates an image indicating the absorption coefficient distribution relative to the pulsed light of the object 706, and displays the generated image on a display 714. The controller corresponds to the processing means of the present invention. The display corresponds to the display means of the present invention.

A user interface 713 is a block for the user to set the operating conditions of the photoacoustic apparatus or giving an operation start instruction. The user interface 713 is configured from a keyboard, a mouse, a button switch and the like. As the operating conditions, there are the measurement range of the object 706 and the measurement time of the photoacoustic signal. Moreover, as the operation instruction, there is the start of photography or end of photography of the object.

The display 714 is a display device for displaying the diagnostic image and notifying the status of the photoacoustic apparatus to the user.

The controller 712 is connected to the laser controller 701 via a communication cable 715, and is used for setting the laser irradiation parameters, giving irradiation instructions, monitoring the status, and so on.

As the irradiation parameters, there are the number of pulses, light intensity and wavelength of the laser beam that is used for irradiating the object 706. The user can set the irradiation parameters via the user interface 713. Moreover, as the contents of the irradiation instructions, there are the start of warming-up and start of laser irradiation, and the user can control the operation of the light source via the user interface.

Moreover, as the monitoring of the statue, there is the monitoring of the value of the irradiation light intensity for each pulse measured by the actinometer 124. When this light intensity is transmitted to the controller 712 via the communication cable 715, the signals can be corrected. Moreover, the status of the processor 105 can be transmitted to the controller 712 and displayed on the display 714.

(Processing Flow)

Figure 8:
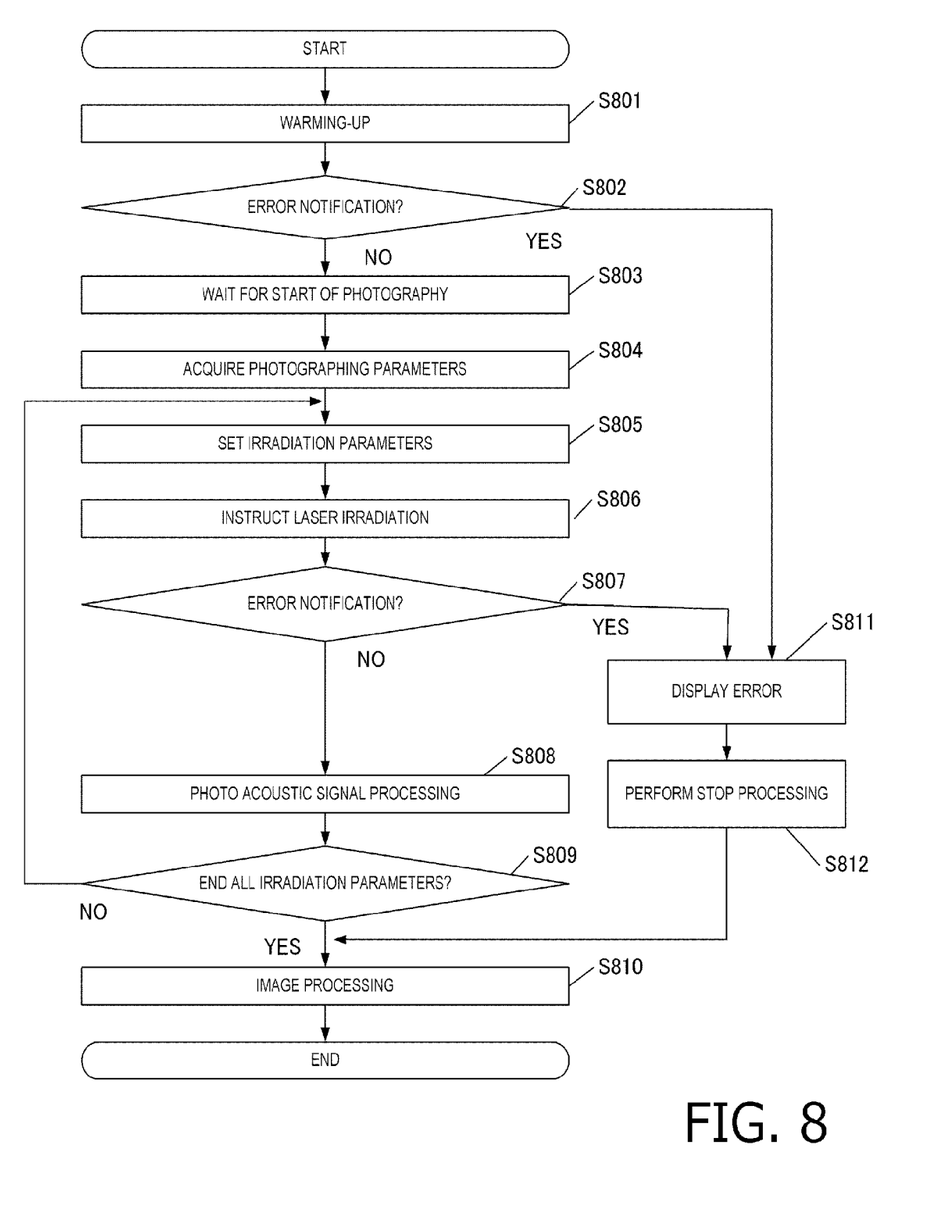
FIG. 8 is an operational flowchart in Embodiment 2.

FIG. 8 is a flowchart showing the operational flow of Embodiment 2 of the present invention.

In step S801, the laser controller 701 is causes to start the warming-up. Upon performing the warming-up, the laser controller 701 performs step S201 to step S209 of FIG. 2, activates the temperature control system 705, and stabilizes the temperature of the laser optical system 704. As with Embodiment 1, light is not emitted from the flash lamp 116 until the temperature of the laser medium 117 is stabilized at a high temperature. It is thereby possible to reduce the wear of the flash lamp.

Moreover, an instruction is issued to the laser power source 702 and the PFN 703, and a laser beam is emitted in a state where the shutter 125 is closed, and whether an error is notified is confirmed. The light source is thereby stabilized and the preparations for starting the irradiation of the object 706 are made. When an error was not notified while the laser controller 701 was performing the warming-up in step S802 (S802=NO), the routine proceeds to step S803. When an error was notified (S802=YES), the routine proceeds to step S811.

In step S803, the user sets the photographing parameters through the user interface 713, and waits to give the irradiation start instruction. During this period, the user sets the object 706 at a position where light can be irradiated using a holding mechanism not shown. Since the object 706 is a part of the human body, it may take time until preparations for photography are complete for changing, other diagnosis, medical examination, and so on. In the foregoing case, while much time is required for step S803, since the laser controller 701 has stopped the emission of the flash lamp in step S208, the wear of the flash lamp can be suppressed.

Subsequently, in step S804, the controller 712 reads the photographing parameters and stores them in the internal memory. As the photographing parameters, there are the irradiation range of the object 706 to be irradiated with the laser beam, and the list of wavelengths of the laser beam to be irradiated. In this embodiment, the two wavelengths of 756 nm and 797 nm are selected as the irradiation wavelengths, and 100 pulses each are to be irradiated with the respective wavelengths. In the foregoing case, 756 nm is the first wavelength, and 797 nm is the second wavelength.

Subsequently, in step S805, the controller 712 sends to the laser controller 701 the irradiation parameters pertaining to the light source among the photographing parameters. The irradiation parameters sent to the laser controller 701 the first time are the wavelength (756 nm) and the number of irradiations (100 pulses).

Subsequently, in step S806, the controller 712 sends an instruction to the laser controller 701 for starting the irradiation of the laser beam. Consequently, pulsed light of 756 nm is irradiated 100 times for irradiating the object 706 according to the routine of step S210 to step S214 of FIG. 2. In step S212 midway during the routine, when it is determined that the light intensity cannot be stabilized even when sufficient warming-up is performed, in step S214, an error is notified from the laser controller 701 to the controller 712.

In step S807, the controller 712 determines whether an error was notified. When an error was not notified (S807=NO), the routine proceeds to step S808. When an error was notified (S807=YES), the routine proceeds to step S811.

In step S808, the receiving circuit 711 performs signal processing such as amplification, A/D conversion and noise reduction to the photoacoustic signals obtained as a result of the probe receiving the photoacoustic waves 709 that are generated for each irradiation of the pulsed light, and thereafter stores the results in the internal memory.

In step S809, the controller 712 determines whether the acquisition of the photoacoustic signals based on all designated irradiation parameters is complete. When incomplete (S809=NO), the routine returns to step S805, and the subsequent irradiation parameters are designated to the laser controller 701. In this embodiment, while the first irradiation was based on the wavelength of 756 nm, since the irradiation based on the wavelength of 797 nm has not yet been performed, the routine returns to step S805, and the number of irradiations based on the wavelength of 797 nm is set to 100 times. After the acquisition of the photoacoustic signal based on both wavelengths of 756 nm and 797 nm, the routine proceeds to step S810 (S809=YES).

In step S810, the controller 712 reads the photoacoustic signal data stored in the memory, performs image processing such as image reconfiguration processing and scan conversion processing, displays the photoacoustic image on the display 714, and then ends the processing. Here, it is also possible to display photoacoustic images of a plurality of wavelengths next to each other according to the user's instructions via the user interface 713, or estimate the oxygen saturation of the blood hemoglobin based on the difference in the light absorption distribution for each wavelength and displaying the result.

Meanwhile, when an error was not detected by the laser controller 701 during the warming-up and the laser light irradiation, in step S811, an error message is displayed on the display 714 for warning the user. Subsequently, in step S812, the controller 712 sends an instruction to the laser controller 701, and stops the laser power source 702, the PFN 703, the laser optical system 704, and the temperature control system 705.

As described above, emission of the flash lamp is reduced during the warming-up process and the photography standby process, which take time, in the operational flow of the photoacoustic apparatus in order to reduce the wear of the flash lamp. It is thereby possible to reduce the frequency of replacing the flash lamp, and provide a photoacoustic apparatus with low maintenance cost and high availability.

As described above, according to the present invention, the number of emissions of the flash lamp during the warming-up operation can be minimized. It is thereby possible to reduce the wear of the flash lamp and extend the life of the light source.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-133910, filed on Jun. 26, 2013, which is hereby incorporated by reference herein in its entirety.

What is claimed is:

1. A laser apparatus, comprising:
a laser medium;
temperature controlling means configured to control a temperature of said laser medium, and including a circulator circulating a substance near said laser medium to heat the laser medium, and heating means heating said substance circulating within said circulator;
excitation means configured to excite said laser medium;
control means configured to control said temperature controlling means and said excitation means;
first temperature measuring means configured to measure the temperature of said laser medium; and
second temperature measuring means configured to measure a temperature of said substance circulating within said circulator,
wherein said control means does not activate said excitation means until the temperature of said substance circulating within said circulator, measured by said second temperature measuring means, reaches a first value, and activates said heating means until the temperature of said laser medium, measured by said first temperature measuring means, reaches a second value different from said first value,
wherein a current to flow to said heating means after the temperature of said substance circulating within said circulator, measured by said second temperature measuring means, reaches the first value and until the temperature of said laser medium, measured by said first temperature measuring means, reaches the second value, is smaller than a current to flow to said heating means until the temperature of said substance circulating within said circulator, measured by said second temperature measuring means, reaches the first value.

2. The laser apparatus according to claim 1, wherein said second value is higher than said first value.

3. The laser apparatus according to claim 1, further comprising:
a light intensity measuring means configured to measure a light intensity of a laser beam,
wherein said light intensity measuring means measures the light intensity of the laser beam after said control means activates said excitation means and before an object is irradiated with the laser beam.

4. The laser apparatus according to claim 3, wherein, if the light intensity of the laser beam measured by said light intensity measuring means in a prescribed period is within a predetermined range, said control means stops light emission of the excitation means until an object is prepared.

5. The laser apparatus according to claim 3, wherein, if the light intensity of the laser beam measured by said light intensity measuring means in a prescribed period is not within a predetermined range, said control means provides notification of an error.

6. The laser apparatus according to claim 1, wherein said control means performs control so that peaks of power consumption of said heating means do not overlap with peaks of power consumption of said excitation means.

7. The laser apparatus according to claim 1, wherein said excitation means is a flash lamp, and
wherein said control means causes simmer current to flow to said flash lamp if preparation time of the object is equal to or shorter than a predetermined period, and stops the simmer current if the preparation time of the object is longer than the predetermined period.

8. The laser apparatus according to claim 1, wherein said laser medium comprises alexandrite.

9. An object information acquiring apparatus, comprising:
said laser apparatus according to claim 1;
a probe configured to receive acoustic waves that are generated when an object is irradiated with the laser beam from said laser apparatus; and processing means configured to acquire characteristic information relating to the object in use of the acoustic waves.

* * * * *